United States Patent [19]

Gabriele et al.

[11] Patent Number: 4,691,333
[45] Date of Patent: Sep. 1, 1987

[54] BREAST COMPRESSION AND NEEDLE LOCALIZATION APPARATUS

[76] Inventors: Joseph M. Gabriele, 846 Carole La., Fenton, Mich. 48430; George J. Sam, Sr., 22306 Grove Pt., St. Clair Shores, Mich. 48081; John N. Wolfe, 4707 E. St. Antoine, Detroit, Mich. 48210; Navinchandra J. Parekh, 3159 Middlebury La., Birmingham, Mich. 48010

[21] Appl. No.: 817,568

[22] Filed: Dec. 27, 1985

[51] Int. Cl.⁴ .................. A61B 6/04; A61B 10/00; G03B 42/02; H05G 1/28
[52] U.S. Cl. ...................... 378/37; 128/754; 128/303 B; 269/328; 378/164; 378/180; 378/208
[58] Field of Search .......... 378/37, 180, 208, 164, 378/162; 128/754, 303 B; 269/328

[56] References Cited

U.S. PATENT DOCUMENTS

| | | | |
|---|---|---|---|
| 3,526,222 | 9/1970 | Dreibelbis | 378/208 |
| 3,547,121 | 12/1970 | Cherry | 378/164 |
| 3,817,249 | 6/1974 | Nicholson | 128/303 B |
| 4,007,732 | 2/1977 | Kvavle et al. | 378/37 |
| 4,034,224 | 7/1977 | Heavens et al. | 378/208 |
| 4,563,768 | 1/1986 | Read | 378/180 |

OTHER PUBLICATIONS

Yagan et al, "Mammographic Needle Localization of Lesions Seen in Only One View", *AJR*, 144: 911–916, May, 1985.

*Primary Examiner*—Craig E. Church
*Assistant Examiner*—T. N. Grigsby
*Attorney, Agent, or Firm*—Cullen, Sloman, Cantor, Grauer, Scott & Rutherford

[57] ABSTRACT

A breast compression plate is connected to a cartridge sleeve for containing a mammographic film cartridge with adjustable tension in a range of positions with detachable straps. The plate is a semi-rigid planar member having a plurality of perforations disposed in a matrix for locating a needle used to determine the position of breast lesions. The plate has spaced buckles which are secured to the straps. The straps have a series of loops formed on one side which are gripped by a plurality of closely spaced hooks secured to spaced ends of the cartridge sleeve. The series of loops extend along the length of the straps to permit changing the length of the straps extending between the plate and the cartridge sleeve, thereby permitting lateral positioning and tension adjustment. The plurality of hooks extend across the cartridge sleeve generally perpendicular to the length of the straps on opposite ends of the sleeve to permit positioning of the plate perpendicularly relative to the length of the straps.

20 Claims, 5 Drawing Figures

BREAST COMPRESSION AND NEEDLE LOCALIZATION APPARATUS

BACKGROUND OF THE INVENTION

I. Technical Field

The present invention relates to mammographic equipment. More particularly, the present invention relates to a breast compression apparatus having a perforation matrix through which a needle is inserted to identify the location of breast lesions.

II. Background Art

Special roentgenography, or x-ray, techniques for photographically studying the mammary gland, or breast, have resulted in more frequent success in detecting small, non-palpable breast lesions that require excisional biopsy. Breast lesions detectable by x-ray techniques may include carcinoma, calcification, proliferative changes, fibroadenomas, fibrocystic changes or normal tissues. Biopsy of lesions in the initial non-palpable phase is vital to improving treatment effectiveness.

If mammograms reveal a suspicious non-palpable lesion, they may be followed up by a localization procedure which is performed shortly before surgery. The localization procedure generally includes compressing the breast having the non-palpable lesion in a vice-like compression device having a perforation grid. A needle is inserted through one of the perforations and an x-ray is taken with the needle implanted in the general vicinity of the lesion. The x-ray film is then developed while the patient remains in the breast compression device until it is determined whether the needle is accurately placed at the lesion. If the initial location is wrong, the needle is re-implanted and the process is repeated until the lesion is located. Due to the pain and length of time that the breast must be maintained in the compression device, only two or three attempts to locate the lesion are generally tolerable in a single session. When the lesion is located by the needle, a J-shaped marker wire may be inserted through the needle to encircle the lesion. The needle may then be removed and the biopsy performed by a surgeon using the marker wire as a guide to locate and excise the lesion.

Breast compression devices may be applied to permit a medial, or lateral, approach or more usually cranial, or vertical, approach. In either, the breast must remain stationary relative to the perforation grid which necessitates that the patient stay in a fixed position while the localization technique is performed and the x-ray film is developed. If two or more insertions are required, remaining immobile can become increasingly uncomfortable.

An example of a compression device used in needle localization is described in Tabar, Laszlo and Peter V. Dean, "The Investigation of Lesions of the Breast", American Clinics of North America, Vol. XVII No. 3 (December 1979), pp. 616–7. The compression plate for preoperative localization of breast lesions disclosed therein comprises a rigid "Plexiglass", a trademark of Rohm and Haas, for thermoplastic polymethyl methacrylate-type polymers, plate which is held by mechanical claping means between the compression plate and a base plate. Both the compression plate and the base plate are secured to the mammographic equipment and the patient is expected to remain immobile during the localization procedure.

A further development of compression devices for preoperative localization is described in Goldberg, Ronald P., Ferris M. Hall, Morris Simon, "Preoperative Localization of Non-Palpable Breast Lesions Using a Wire Marker and Perforated Mammographic Grid", Radiology 146:833–835, March 1983. The compression device disclosed therein has a perforated grid comprising a freestanding apparatus made of "Plexiglass" that is usable with standard mammographic x-ray equipment. Two base plates form a tunnel into which mammographic film can be inserted while the breast is held compressed. The breast is positioned between the tunnel and the upper "Plexiglass" plate which has multiple perforations that are arranged as a centimeter grid. Some of the perforations are marked with a lead-containing paint so that they can be identified both visually and radiographically. The top plate may be adjusted to change the amount of compressive force applied and to allow for breasts of different sizes. The top plate is fixed in position by a set of detachable bull dog clamps that attach to four threaded rods extending upwardly from the base plates. The device is usable in either the lateral or cranial orientation.

The primary disadvantage with the above devices is their rigidity and the lack of comformability of the pressure plate which results in discomfort. Clamp or vice-like compression force applying mechanisms also add to discomfort and rely solely upon the application of compression to prevent slippage. The compression plate and base generally are smooth planar members that do not conform to the body. Movement of the breast within the compression device is a serious problem, especially if the compression force is not sufficient.

The breast compression and needle localization devices should be sterilized between uses, at least those portions which contact the breast. If the breast compression device is an integral part of the mammographic equipment, sterilization requires disassembly of the device from the machine. Sterilization of the perforated needle localization plate is particularly important and cannot be done without disassembly of the equipment.

Another disadvantage of breast compression and needle localization devices which are incorporated as an integral part of the mammographic equipment is that the patient must remain at the machine during the plate development process and usage of the machine cannot be shared with other patients.

These and other disadvantages are overcome and problems are solved by the present invention's provision of an improved breast compression apparatus including a needle localization matrix as summarized below.

SUMMARY OF THE INVENTION

According to the present invention, a breast compression device for use in mammographic radiological investigations is provided wherein a sleeve and breast compression plate are interconnected by first and second straps. The sleeve has an opening for receiving a mammographic film cartridge. The breast compression plate has a plurality of perforations which are preferably disposed in a matrix of closely spaced perforations. The straps used to interconnect the sleeve to the plate are flexible, with each strap being secured on one end to the plate at spaced locations on the plate and are secured on their other end to spaced anchoring locations on the sleeve. The length of the straps extending between the plate and the sleeve may be adjusted to exert a biasing or compressive force against a breast located between the plate and the sleeve.

The straps may be anchored to the sleeve in a range of locations to permit the positioning of the plate relative to the sleeve. In the illustrated embodiment, the straps are detachably connected to the sleeve.

The straps preferably include a first interengaging surfaces and the sleeve includes second interengaging surface complementary to the first interengaging surfaces at the spaced anchoring locations whereby the first and second interengaging surfaces may be detachably secured to one another in a range of locations to adjust the location and compressive force applied by the plate. The first interengaging surfaces on the straps preferably extend along the length of the straps and the second interengaging surfaces on the sleeves extend in a direction generally perpendicular to the length of the straps. The first and second interengaging surfaces are preferably "Velcro" fasteners wherein one of said surfaces includes a plurality of loops forming a felt-like surface and theother interengaging surface comprises a plurality of closely spaced hooks which are adapted to detachably grip the loops of the other interengaging surface. "Velcro" is a registered trademark of Velcro U.S.A.

According to another aspect of the present invention, the breast compression device includes a cartridge sleeve adapted to receive a mammographic film cartridge having an upper plate with a textured upper surface, a laminated base plate and first and second sides connecting the upper plate to the base plate.

The device further includes a compression plate comprising a semi-rigid planar member having a plurality of perforations formed in a grid pattern. The compression plate includes buckles at spaced points thereon which have an arcuate bar on the exterior sides thereof upon which first and second straps are detachably secured.

The straps are secured to the cartridge sleeve by means of first and second interengaging means formed on the straps at a spaced point from the buckles. The straps are detachable from the sleeve at the interengaging means to permit adjustment of the length of the first and second straps which extend between the sides of the cartridge sleeve and the plate. The straps may also be positioned by attaching the straps to the sleeve in a range of locations perpendicular to the length of the straps.

The ability of the apparatus to hold the breast in place in the apparatus is enhanced by the inclusion of textured surfaces on the sides of the sleeve and plate which contact the breast. Also, the top plate is semi-rigid permitting it to conform to a limited extend to the breast.

The apparatus of the present invention is easy to attach and may be quickly and accurately applied to a breast. The "Velcro" fasteners permit the straps to be firmly secured to the sleeve with sufficient compressive force to hold the breast stationary within the apparatus, especially since the surfaces in contact with the breast are textured and the plate is intended to conform to a limited extent to the breast. The straps are flexible which allows for maximum versatility in applying the device to a broad range of breast sizes.

Another important advantage of the apparatus of the present invention is that the apparatus may be easily disassembled and sterilized by merely disconnecting the "Velcro" straps and soaking the components in an antiseptic solution. The plate and sleeve are formed of a polymeric material that is strong yet lightweight and easy to maintain in a clean and sanitary condition.

These and other advantages of the present invention will become more apparent upon studying the attached drawings in view of the following specification and claims.

DETAILED DESCRIPTION OF THE INVENTION

Figure 1:
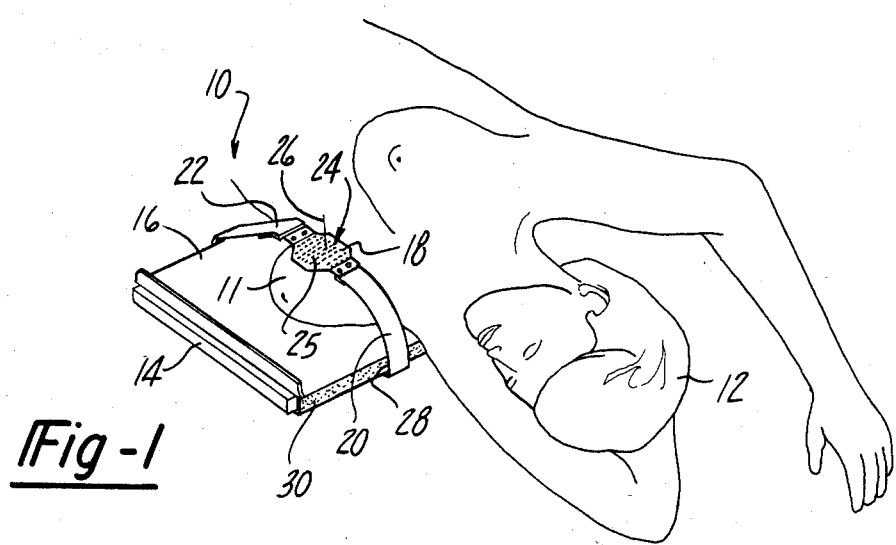
FIG. 1 is a perspective view showing the breast compression and needle localization apparatus of the present invention attached to a patient for lateral needle insertion.
Figure 2:
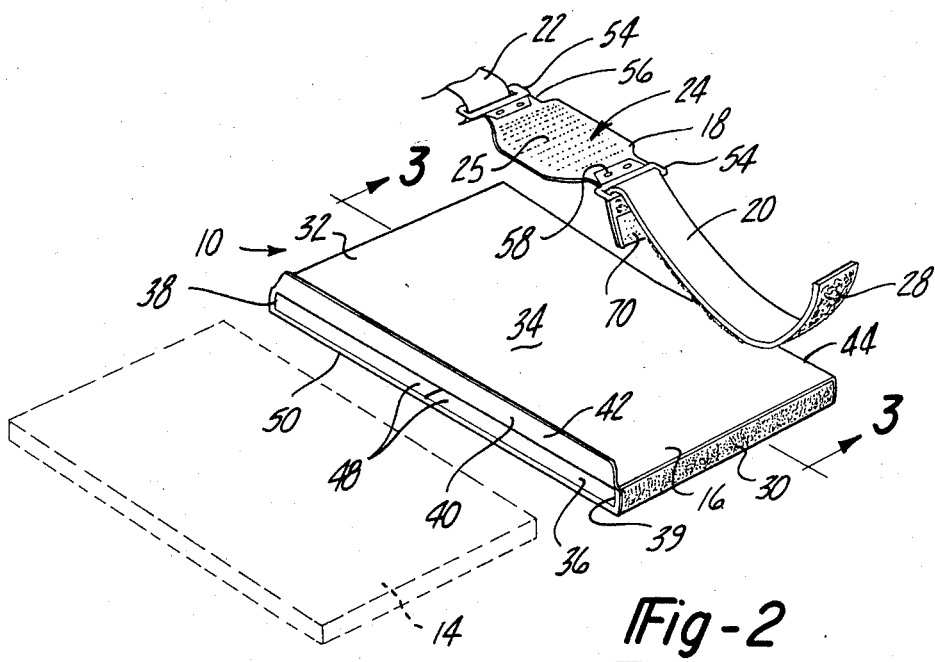
FIG. 2 is an exploded perspective view of the apparatus of the present invention also showing a mammographic film cartridge in phantom.
Figure 4:
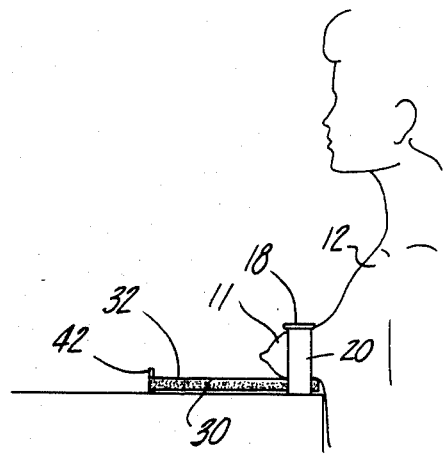
FIG. 4 is a side elevational view of the apparatus of the present invention attached to patient for vertical needle insertion.

Referring now to FIGS. 1, 2 and 4, the breast compression device of the present invention is generally indicated by reference numeral 10. The breast compression device 10 is shown attached to the breast 11 of a patient 12. An x-ray film cartridge 14 is shown inserted in a cartridge sleeve 16 on the exterior lateral side of one breast 11. A compression and needle locating plate 18 is biased into engagement with the interior side of the breast 11 by first and second straps 20 and 22. The plate 18 includes a perforation matrix 24 which includes a plurality of closely and evenly spaced perforations 25. The perforations 25 are adapted to receive a needle 26 which is inserted through the plate 18 into the breast 11 at the suspected location of a non-palpable lesion.

The first and second straps 20 and 22 preferably comprise a strip of "Velcro" material which is adapted to be secured to a complementary strip of "Velcro" material attached to the cartridge sleeve 16. In the illustrated embodiment, the straps 20, 22 are either made up of or have attached thereto the loop tape 28 portion of the "Velcro" fastener. The hook tape 30 of the "Velcro" fastening system is preferably secured to the cartridge sleeve 16. The loop tape 28 is the felt-like portion of the "Velcro" fastening system and the hook tape 28 is the portion of the fastening system having a series of closely spaced barbs or hooks.

Figure 3:
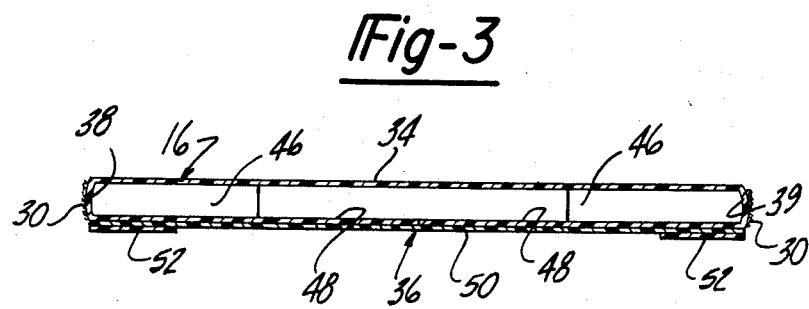
FIG. 3 is a cross-sectional view taken along the line 3—3 in FIG. 2.

Referring now to FIGS. 2 and 3, the components of the breast compression device are shown in greater detail. The cartridge sleeve 16 is preferably formed of a low atomic weight molded plastic having a low level of x-ray attenuation. Most preferably, the cartridge is formed of a polystyrene material such as "Royalite 24", a trademark of Rohm and Haas. However, it is anticipated that the cartridge may be formed of an acrylic, polyethylene or polyvinyl.

The cartridge sleeve 16 includes an upper plate 32 which extends across the top of the film cartridge 14. The upper plate 32 has an upper surface 34 which is preferably textured to reduce the tendency of a breast to slide thereon. The cartridge sleeve 16 includes a base plate 36 disposed on the opposite side of the film cartridge 14 from the upper plate 32. The upper plate 32 and base plate 36 are interconnected by first and second side plates 38 and 39. First and second side plates 38 and 39 are preferably reinforced or formed to be slightly thicker than the upper plate 32.

A front opening 40 is formed in the sleeve 16 through which the cartridge 14 is received. A lip 42 is formed adjacent the front opening 40 to aid in insertion and removal of the cartridge 14 in the sleeve 16. The rear edge 44 of the sleeve 16 is preferably concave to facilitate placement of the cartridge sleeve 16 against the body of the patient 12 in either the vertical or horizontal plane. Spacers 46, as shown in FIG. 3, are preferably placed at the rear edge 44 of the cartridge 16 to both space the base plate 36 relative to the upper plate 32 and to provide an end stop for insertion of the cartridge 14 in the sleeve 16.

The base plate 36 is preferably a rigid reinforced supporting surface. The base plate in the illustrated embodiment includes reversely bent flanges 48 extending inwardly from each of the first and second sides 38 and 39 to the middle of the base plate 36. The reversely bent flanges 48 are secured together by means of a reinforcement lamination 50 which is adhesively secured to the flanges 48. The upper plate 32, first and second sides 38 and 39 and reversely bent flanges 48 are all preferably formed in one piece as an integral molded part having molded corners. The reinforcement lamination 50 is preferably formed of the same material as the other portions of the sleeve 16.

Non-skid elastomeric feet 52 may be secured to the bottom of the base plate 36 to aid in positioning the sleeve 16 relative to the x-ray machine so that it will not slide during preparations for or the taking of x-rays.

Figure 5:
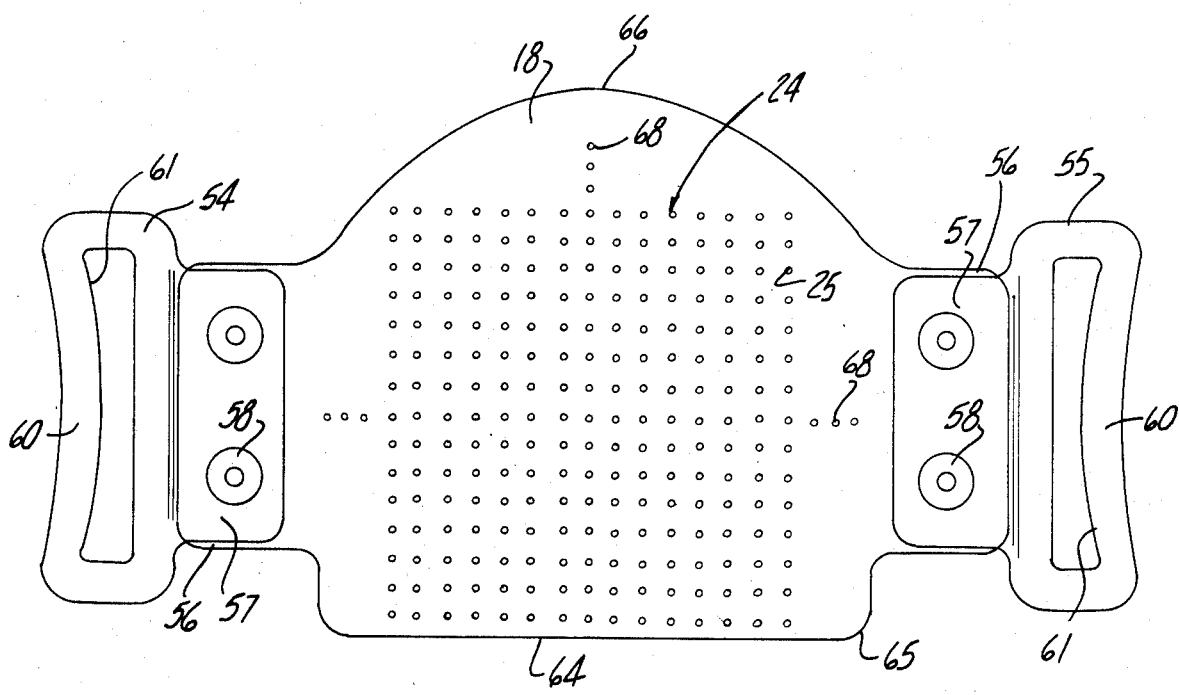
FIG. 5 is a plan view of the breast compression plate having a matrix of needle localization perforations and including the first and second buckles on opposite ends thereof.

Referring now to FIGS. 2 and 5, the compression plate and needle localization plate 18 will be described in greater detail. It is preferred that the plate 18 be formed of the same material as the sleeve 16 and that its lower surface is textured similar to the top of the sleeve 16 to prevent relative movement of the breast therebetween. The plate 18 includes first and second buckles 54 and 55 which are secured to first and second buckle flanges 56 and 57 which are formed integrally with the plate 18. First and second buckles 54 and 55 are connected to first and second buckle flanges 56 and 57 by means of rivets 58 or other fasteners.

As shown in FIG. 5, the buckles 54, 55 each include an arcuate bar 60 on their exterior ends which includes a convex cylindrical surface 61 over which the straps 20, 22 are secured. The convex cylindrical surface 61 of the arcuate bar 60 permit the straps to exert a pulling force in a range of angular directions relative to the plate 18. This is an important feature since the contour of bodies of different patients vary substantially and the breast compression device must be versatile to accommodate different body shapes.

The plate has a rear edge 64 which is preferably radiused and has curved corners 65 at opposite ends. The rear edge 64 is radiused and the corners 65 curved for the comfort of the patient. The front edge 66 of the plate 18 is preferably contoured to reflect the shape of a compressed breast 11 as a guide to the proper application of the device.

The plate 18 includes indicator perforations 68 at the midpoint of the perforation matrix 24 which facilitate counting perforations if necessary to change the perforation through which the needle 26 is inserted. By using the indicator perforation 68, the perforation matrix 24 may be broken into four quadrants, thereby reducing the number of perforations that must be counted to locate a particular perforation 25.

The straps 20, 22 are preferably connected to the buckles 54, 55 by threading the strap through the buckle and reversely bending the strap. Preferably, the entire strap length includes the loop tape 28 whereby when the strap is doubled back, a coupler 70 comprising a double-faced member formed of the "Velcro" hook tape 30 is used to secure the strap around the buckle.

In operation, the breast compression device 10 of the present invention is placed on a supporting surface which may either be a table or a stretcher and the breast 11 of the patient 12 is laid on the cartridge sleeve 16. The plate 18 is then placed on the opposite side of the breast from the sleeve 16 and first and second straps 20 and 22 are pulled outwardly to anchor the loop tape 28 of the straps to the hook tape 30 on the first and second sides 38 and 39 of the sleeve 16. It should be noted that the hook tape 30 extends across the width of the sleeve 16 to permit the straps 20, 22 to be secured anywhere along the length of the hook tape 30. In this way, widely varying body sizes may be accommodated by the same apparatus. It is anticipated that more than one size of plate 18 will be provided to accommodate varying breast sizes. The arcuate bar 60 of the buckles 54, 55 further aids in aligning the plate 18 relative to the breast 11 and sleeve 16.

The straps 20, 22 are pulled to exert a compressive force on the breast 11 by the plate 18. The straps 20, 22 may also be tightened from the plate end of the strap if more convenient by merely reattaching the coupler 70 from the loop tape 28 of the straps. The plate 18 is semi-rigid and will conform to a limited extent to the shape of the breast 11 as the straps 20, 22 pull down upon the ends of the plate 18. If the straps 20, 22 are formed of the loop tape 28 or include loop tape 28 across their entire length, the amount of compression and length of the straps may be adjusted by simply detaching the straps from the hook tape 30 and refastening the loop tape 28 at a different point to the hook tape 30.

Once the breast compression device 10 is attached to the patient's breast 11, the film cartridge 14 may be inserted in the front opening 40 of the cartridge sleeve 16 and exposed to the gamma rays of standard x-ray equipment. A preliminary x-ray may be taken of the breast after attachment of the device 10 and the lesion may be located by inserting a needle through the perforation 25 and the perforation matrix 24 located closest to the lesion. After the needle is inserted, another x-ray may be taken to determine whether or not the needle has been inserted at the lesion. If this is accomplished, a marker wire may be inserted through the needle and implanted in the breast adjacent the lesion to guide a surgeon to the proper location in the breast for the excisional biopsy. If the initial needle placement is not accurate, another perforation 25 may be selected by merely counting from the needle perforation 25 to the desired closer perforation.

After the lesion has been located and marked as appropriate, the breast compression device 10 may be removed and sterilized. Sterilization is accomplished merely by soaking the sleeve 16, plate 18 and first and second straps 20, 22 in a suitable antiseptic solution. The device of the present invention can be used repeatedly, and, if necessary, the straps may be replaced or repaired if the "Velcro" becomes worn.

The above description of a new, improved breast compression and needle localization apparatus is intended as an example and not in a limiting sense. It will be appreciated that the component parts, materials and relative dimensions given above may be modified without departing from the spirit and scope of the invention. The scope of the invention is to be determined based upon the full scope of the following claims and all equivalents thereof.

I claim:

1. A breast compression device for use in mammographic radiological investigations comprising:
    a sleeve made of a material having a generally low level of x-ray attenuation and having an opening adapted to receive a mammographic film cartridge;
    a breast compression plate made of a material having a generally low level of x-ray attenuation and having a plurality of perforations disposed in a matrix;
    first and second flexible straps extending between and interconnecting said plate and said sleeve, said straps each being secured on one end to spaced locations on said breast compression plate and each of said straps being secured at spaced anchoring locations to said sleeve; and
    adjustment means included on at least one of said straps for adjusting the length of said straps extending between said plate and said sleeve and biasing said plate towards said sleeve to compress at least one breast between said plate and said sleeve.

2. The breast compression device of claim 1 wherein said straps include positioning means for changing the anchoring locations at which said straps are secured to said sleeve.

3. The breast compression device of claim 2 wherein said positioning means and said adjustment means are combined in a detachable connector provided on at least one of said straps.

4. The breast compression device of claim 1 wherein said straps each respectively include a first interengaging surface and said sleeve includes a second interengaging surface at said spaced anchoring locations, said first and second interengaging surfaces being detachably secured to one another in a range of locations such that said adjustment means is provided.

5. The breast compression device of claim 4 wherein said first interengaging surface extends longitudinally along said straps.

6. The breast compression device of claim 5 wherein said second interengaging surface extends across said sleeve in a direction generally perpendicular relative to the longitudinal extension of said first interengaging surface, such that said positioning means is provided.

7. The breast compression device of claim 4 wherein said first interengaging surface comprises a surface having a plurality of loops and said second second interengaging surface comprises a surface having a plurality of hooks adapted to be detachably secured to said loops.

8. The breast compression device of claim 1 wherein said breast compression plate includes indicator perforations extending outwardly from the perforation matrix.

9. The breast compression device of claim 1 wherein said breast compression plate is secured to said first and second straps by buckles secured to the plate about which said straps are secured.

10. The breast compression device of claim 9 wherein said buckles include an arcuate bar on their outer ends for engaging said straps in a range of angular orientations.

11. A breast compression device for use in mammographic radiological preoperative investigation techniques comprising:
    a cartridge sleeve made of a material having a generally low level of x-ray attenuation, adapted to receive a mammographic film cartridge and having an upper plate with a textured upper surface, a laminated base plate, first and second sides connecting said upper plate to said base plate, first and second spacers connecting said upper plate to said base plate at one end of said first and second sides;
    a compression plate being a semi-rigid planar member made of a material having a generally low level of x-ray attenuation and having a plurality of perforations formed in a grid pattern;
    first and second buckles secured on an inner side to opposite ends of said planar member, said buckles having an arcuate bar on an outer side thereof;
    first and second flexible straps detachably secured on a first end about the arcuate bar of said first and second buckles respectively; and
    first and second interengaging means formed on a second end of said first and second straps and on each of said first and second sides of said cartridge sleeve respectively for detachably securing said ends of said first and second straps to said first and second sides of said cartridge for adjusting the length of said first and second straps extending between said sides and said plate and for detachably securing said straps to points along the lengths of said sides.

12. The breast compression device of claim 11 wherein said first and second interengaging means comprise complementary multi-position flexible fasteners comprising a hook tape and a loop tape.

13. The breast compression device of claim 11 wherein said first and second sides include reversely bent flanges which are adhesively secured to a reinforcement lamination extending across the length of the sleeve to form the base plate.

14. The breast compression device of claim 11 wherein said upper plate includes a lip located at the front of the sleeve.

15. The breast compression device of claim 11 wherein said upper plate and base plate having a concave rear edge for placing the cartridge sleeve adjacent to a patient's body.

16. The breast compression device of claim 11 wherein elastomeric feet are provided on the base plate to reduce the tendency of the sleeve to move on a supporting surface.

17. A breast compression device for use in mammographic radiological preoperative investigation techniques comprising:
    a plastic cartridge sleeve made of a material having a generally low level of x-ray attenuation adapted to receive a mammographic film cartridge and having an upper plate, a rigid base plate, first and second rigid sides connecting said upper plate to said base plate, first and second spacers connecting said upper plate to said base plate at one end of said first and second sides;
    a plastic compression plate being a semi-rigid planar member made of a material having a generally low level of x-ray attenuation and having a plurality of perforations formed in a grid pattern;

first and second flexible straps extending between the sleeve and the plate;

first and second means secured to opposite ends of said plate for retaining a first end of said first and second flexible straps respectively; and first and second interengaging means formed on a second end of said first and second straps and on each of said first and second sides of said cartridge sleeve respectively for detachably securing said ends of said first and second straps to said first and second sides of said cartridge for adjusting the length of said first and second straps extending between said sides and said plate and for detachably securing said straps to points along the lengths of said sides.

18. The breast compression device of claim 17 wherein said first and second interengaging means comprise complementary multi-position flexible fasteners comprising a hook tape and a loop tape respectively.

19. The breast compression device of claim 17 wherein said first interengaging means extends longitudinally along said straps.

20. The breast compression device of claim 19 wherein said second interengaging means extends across said sleeve in a direction generally perpendicular relative to the longitudinal extension of said first interengaging means.

* * * * *